United States Patent [19]

Klein

[11] Patent Number: 4,930,317
[45] Date of Patent: Jun. 5, 1990

[54] APPARATUS FOR LOCALIZED HEAT AND COLD THERAPY

[75] Inventor: Phillip P. Klein, Plano, Tex.

[73] Assignee: Temperature Research Corporation, Plano, Tex.

[21] Appl. No.: 196,741

[22] Filed: May 20, 1988

[51] Int. Cl.$^5$ .............................................. F25B 21/02
[52] U.S. Cl. ..................................... 62/3.3; 62/259.3; 62/3.5
[58] Field of Search ........................... 62/3, 259.3, 430

[56] References Cited

U.S. PATENT DOCUMENTS

| | | | |
|---|---|---|---|
| 3,080,723 | 3/1963 | Price | 62/259.3 X |
| 3,085,405 | 4/1963 | Frantti | 62/259.3 X |
| 3,136,577 | 6/1964 | Richard | 62/3 X |
| 3,154,926 | 11/1964 | Hirschhorn | 62/3 |
| 3,207,159 | 9/1965 | Tateisi | 62/3 X |
| 3,802,220 | 4/1974 | Pompo | 62/430 X |
| 4,640,284 | 2/1987 | Ruderian | 62/3 X |

*Primary Examiner*—Lloyd L. King
*Attorney, Agent, or Firm*—Alva H. Bandy

[57] ABSTRACT

A hot/cold therapy device includes a hot/cold pad assembly remotely connected to a control module. The hot/cold pad assembly includes a flexible pad filled with a convection (gel) or conduction (laminated metal, rubber impregnated with metal particles, etc.), or combination thereof (a conductive metal layer immersed in a gel). A thin plate of conductive material (copper) forms an extension of the cold plate of a thermoelectric heat pump, both of which are in thermal contact with the pad. An air cooled heat sink of the thermoelectric heat sink is mounted in a housing or shroud, the shroud is connected by a flexible umbilical line to the control module. The control module includes a fan for drawing or blowing air through the shroud to maintain the temperature difference between the heat sink and attached plate of the thermoelectric heat pump element. The control module includes temperature setting and adjust mechanisms together with a display for displaying the pad temperature detected by a temperature sensing transducer. Other embodiments include placement of the fan within the shroud to cool the heat sink, using a water cooled block heat sink connected to a water reservoir, radiator, and water pump contained in the control module together with a fan to cool the radiator. The pad is a conductive gel, laminated metal, metal filled rubber, or metal plate immersed in a gel filled flexible pad.

13 Claims, 5 Drawing Sheets

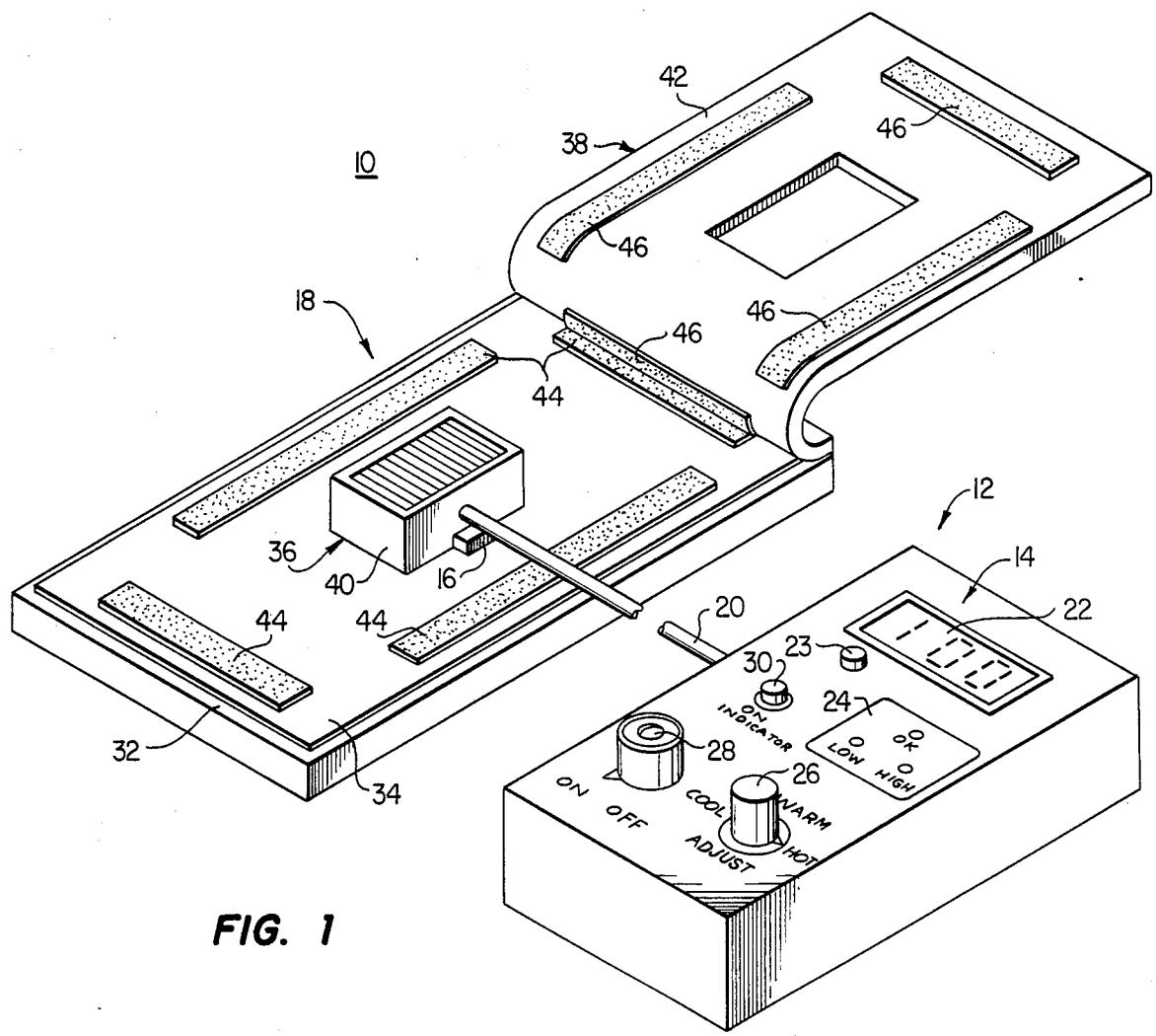
FIG. 1
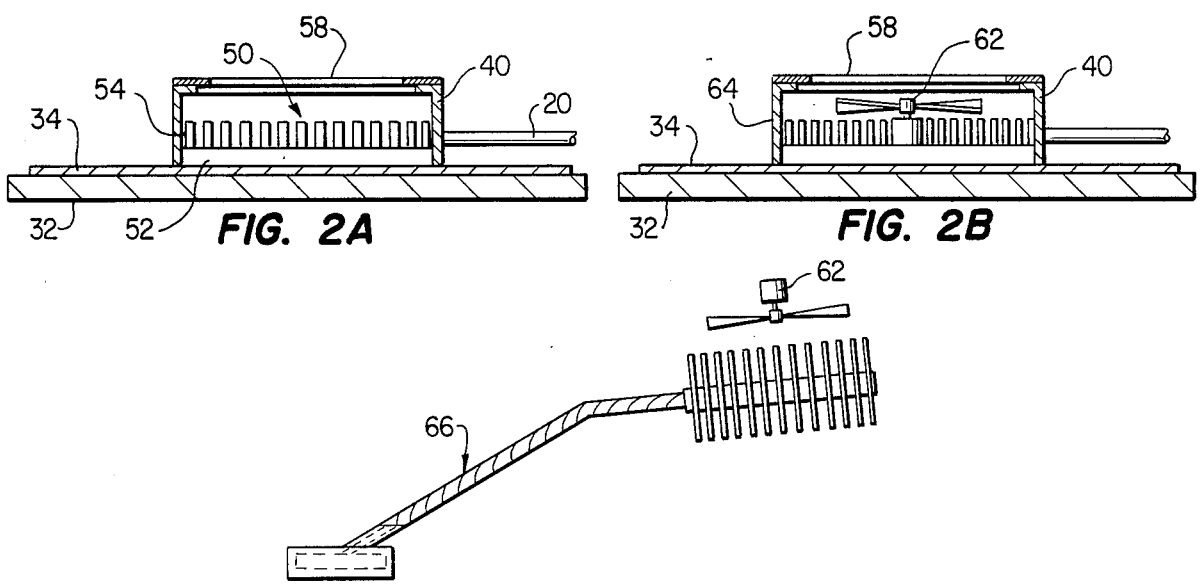
FIG. 2A  FIG. 2B
FIG. 2C

APPARATUS FOR LOCALIZED HEAT AND COLD THERAPY This invention relates to therapeutic device and more particularly to an improved apparatus for localized heat and cold therapy.

BACKGROUND OF THE INVENTION

Electric blankets, heating pads, hot water bottles and ice bags are well known hot/cold localized therapy devices. The electric blankets and heating pads generally have electrical resistance elements incorporated in soft plastic or natural fiber material. Temperature select control switches are provided for controlling the amounts of electrical power applied to the elements. The switch selects power ranges and therefore temperature ranges of the blankets or pads.

Similarly hot/cold therapy devices are used in hospitals; however, these devices are more sophisticated and costly. In these medically approved device,s a hot/cold fluid is circulated through a flexible conduit in the pad to provide a preselected temperature output. The fluid temperature is maintained by three interdependent systems: a refrigeration/heating system, a temperature control system, and a fluid circulating system. The refrigeration/heating system has included a compressor, refrigerant condenser, and evaporating coils for cooling the fluid. Again, heater elements are used where necessary for producing a hot fluid for circulation through the pad's flexible conduits.

More recently, a thermoelectric heat pump has been disclosed as a replacement for the refrigeration/heating system. The temperature control fluid circulating system utilizing the thermoelectric heat pump as the refrigeration/heating system includes a fluid tank having associated therewith at least one thermoelectric heat pump and a temperature sensor. A temperature controller is connected to the temperature sensor and to a power supply. The power supply is connected to the thermoelectric heat pump(s) and is responsive to the temperature control means for supplying power with the appropriate polarity to the thermoelectric heat pump to reach and maintain a selected fluid temperature.

The fluid circulating system includes a pump to force the fluid from the tank through a flexible connecting pipe for circulation through the flexible conduit of the pad and return to the tank through a flexible return pipe.

It is recognized that problems attend the use of a fluid circulation system. One problem is the increased mass which has to be cooled. The mass includes the fluid holding tank, flexible connecting pipes, pad flexible tube, and pad. Thus, to heat the pad to a preselected temperature requires a larger thermoelectric heat pump and more power and time than would be required if only the pad were to be heated.

Another problem is water condensation. Water condensing on the flexible tube of the pad wets the pad; thus, a water proofed pad is required. Water condensing on the flexible interconnecting pipes can drip on the floor creating safety hazards to the patient and to those attending to the needs of a patient. Finally water condensing on the tank can drip into the tank housing to generate rust and electrical shorting problems.

A disadvantage of the known refrigerator/heating system is the bulk of the system. The device is a portable device for movement from one hospital bed side to another, and once positioned occupies substantial bed side space, often in space competition with other required bed side devices.

Another disadvantage of the refrigerator/heating system is the attention required to maintain its proper operation. For example, the fluid tank must be filled and the fluid level maintained for proper operation. Further, the unit must be leveled after each moving for proper operation. Such units generally shut down automatically when tilted more than about eleven degrees. Failure to provide the required attention can result in equipment damage, operation failure, and the creation of safety hazards.

SUMMARY OF THE INVENTION

Accordingly it is an object of the invention to provide an apparatus for localized hot/cold therapy having a substantially reduced mass to be heated/cooled for decreased apparatus cost and operating costs, and rapid heat up and cool down cycle times.

Another object of the invention is to provide a hot/cold therapy apparatus which is substantially free of moisture condensation problems.

A further object of the invention is to provide a hot/cold therapy apparatus of reduced bulk and weight for facilitating its portability.

A further object of the invention is to provide a hot/cold therapy pad for direct application which does not utilize a circulating fluid to effect heat transfer.

Briefly stated the localized heat/cold therapy apparatus constituting the subject matter of this invention consists of a system wherein the temperature is maintained by two interdependent subsystems: a heating/cooling subsystem, and a temperature control subsystem. The liquid support structure and circulating subsystems of known systems have been substantially eliminated.

BRIEF DESCRIPTION OF THE DRAWINGS

Other objects and features of the invention will become more readily understood from the following detailed description when read in conjunction with the drawings in which:

FIG. 1 is an isometric view of the hot/cold therapy device constituting the subject matter of the invention;

FIGS. 2a-2c are partial views of air cooled thermal pad assemblies of the hot/cold therapy device constituting the subject matter of the invention, the views are enlarged to show the details of construction;

DETAILED DESCRIPTION OF PREFERRED EMBODIMENTS OF THE INVENTION

Figure 3A:
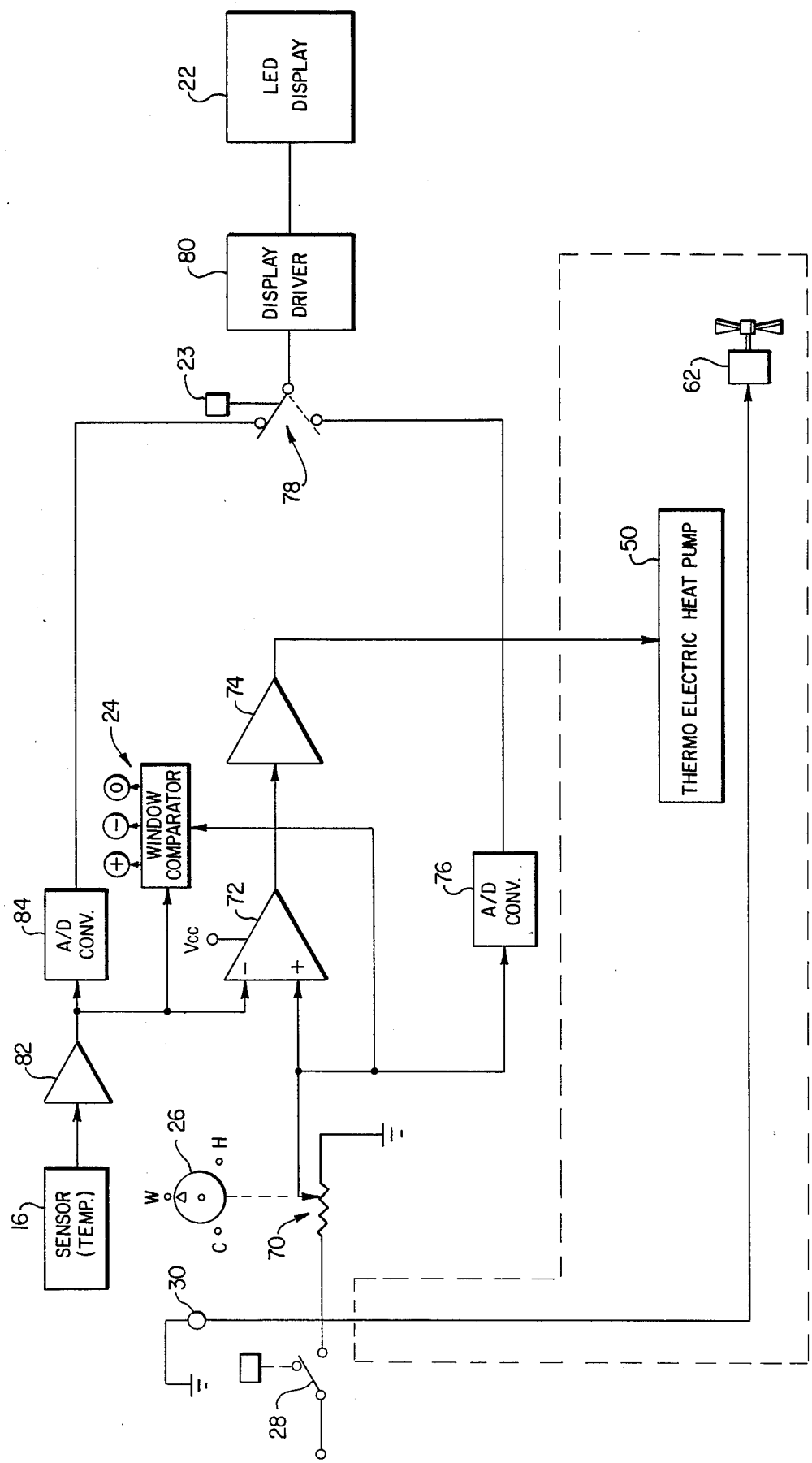
FIGS. 3a-3c are circuit diagrams of the control unit electronics for the various embodiments of the invention.

Referring now to FIG. 1, the hot/cold therapy device 10 constituting the subject matter of the invention includes a control box 12 having a control panel 14, a temperature sensor transducer 16, and a hot/cold thermal pad assembly 18. The control bow 12 is umbilically connected to the thermal pad assembly 18 by an umbilical line (conduit) 20, hereinafter described.

In a first embodiment, the control panel 14 includes a display 22. The display may be either a three digit liquid crystal or light emitting diode display for displaying temperature information. A display switch 23 is provided to display either the selected or actual pad temperature. A temperature status indicator 24 is provided for indicating the operational temperature status. The indicator includes a green light emitting diode for indicating operation at the selected temperature, and a pair of red light emitting diodes for indicating, respectively, temperatures above and below the selected operating temperature. If desired, different colors may be used to indicate temperatures above and below the desired operating temperature. A temperature selection dial 26 is provided for setting and adjusting the temperatures within cooling, warm, and hot temperature ranges. An ON/OFF switch 28 is provided for controlling the on/off operation of the device. The switch preferably may be either a press button or toggle type switch. An on indicator 30 completes the panel of the first embodiment, although it will be appreciated that maintenance indicators may be included for indicating failure of selected components. The on indicator 30 preferably is a light emitting diode.

The hot/cold thermal pad assembly 18 is to provide uniformly heated or cooled areas which are typically larger than the cooling surface of the thermoelectric heat pump. Thus, the pad assembly includes a pad 32 of a size selected for the use application. A thin plate 34 of conductive material can be attached to the pad 32 to extend the cooling area if necessary. A suitable conductive plate is a flexible copper plate having a thickness of about 2 mils. The conductive plate provides an attachment means for connecting the thermoelectric heat pump to the pad and also provides an extension of the hot/cold plate of a thermoelectric heat pump of a hot/cold assembly 36, hereinafter described.

The hot/cold assembly 36 can be either permanently or removably attached to the pad. The pad is secured to the body using the known elastic, rubber or hook and eye loop straps, or provided with hook and loop pile type fastener material such as that sold under the trademark "VELCRO." Velcro is a synthetic material which adheres when two pieces are pressed together. The temperature sensor is attached to the pad at any suitable location, and it is attached to engage the working media of the pad 32. The pad may be of several different types hereinafter described; each of the different types are bendable or shapable to closely conform to the contours and irregular body shapes to which it is applied.

A pad cover 38 corresponding substantially to the shape of the pad encloses the bottom, side,s and all of the top except for the hot/cold assembly housing 40. The cover 38 includes a top portion 42 having an aperture through which the assembly housing 40 protrudes when the top of the pad cover is fastened to enclose the pad 32. A suitable fastener for securing the cover to the pad is preferably a hook, loop pile fastener, which includes patches 44 of VELCRO fixed to the pad's copper plate 34 and positioned to correspond to similar patches 46 fixed to the underneath side of the cover top 42.

Referring now to FIGS. 2a-2c, FIG. 2a discloses a preferred embodiment of the hot/cold assembly 36 of FIG. 1. This preferred embodiment includes the housing 40 containing a thermoelectric heat pump 50 in modular form. The thermoelectric heat pump includes thermoelectric elements 52 having solderable ceramic plates for high electrical insulation and excellent thermal conductivity fixed, respectively, to the pad's conductive plate 34 and to a finned heat sink 54. A grill or louvered aperture 58 is formed in the housing 40 through which air at ambient temperature is either drawn or blown across the finned heat sink 54. If drawn the air flow is from the heat sink, through a conduit formed in the conduit 20, and out a grill 60 (FIG. 4) of the control box 12 by a fan 62 (FIG. 3a). The fan 62 is mounted in the control box 12. The umbilical line 20 also houses the electrical leads for the thermoelectric heat pump 50 and temperature sensor 16.

FIG. 2b discloses another embodiment of the hot/cold assembly 34. This embodiment is substantially that of FIG. 2a except that the assembly housing 40 has an exit grill 64 formed in a side wall, and the fan 62 (including motor and fan blades) is mounted in the assembly housing 40 to draw air through grill 58, across the heat sink 56 and out the grill 64.

FIG. 2c discloses still another embodiment of the hot/cold assembly 34. The FIG. 2c embodiment is substantially different from the preceding embodiments in that it includes a flexible heat pipe 66 having a cold/hot end connected to the pad's conductive plate 34 and a finned hot/cold end mounted in the control box 12 (FIG. 4) adjacent the fan 62. The control box 12 further includes an air inlet grill 68. Thus, air is drawn through the inlet grill 68, across the finned h to/cold end of the heat pipe, and out the grill 60 by the fan 62 to maintain the finned hot/cold end substantially as ambient temperature. Alternatively, the heat pipe 66 can be constructed so that the fan 62 is eliminated but still result in substantially equivalent performance with the additional advantage of silent operation. By structuring a higher performance heat pipe and placing the finned end outside the control box 12 normal air movement is sufficient to maintain the finned hot/cold end substantially at ambient temperature.

Figure 3B:
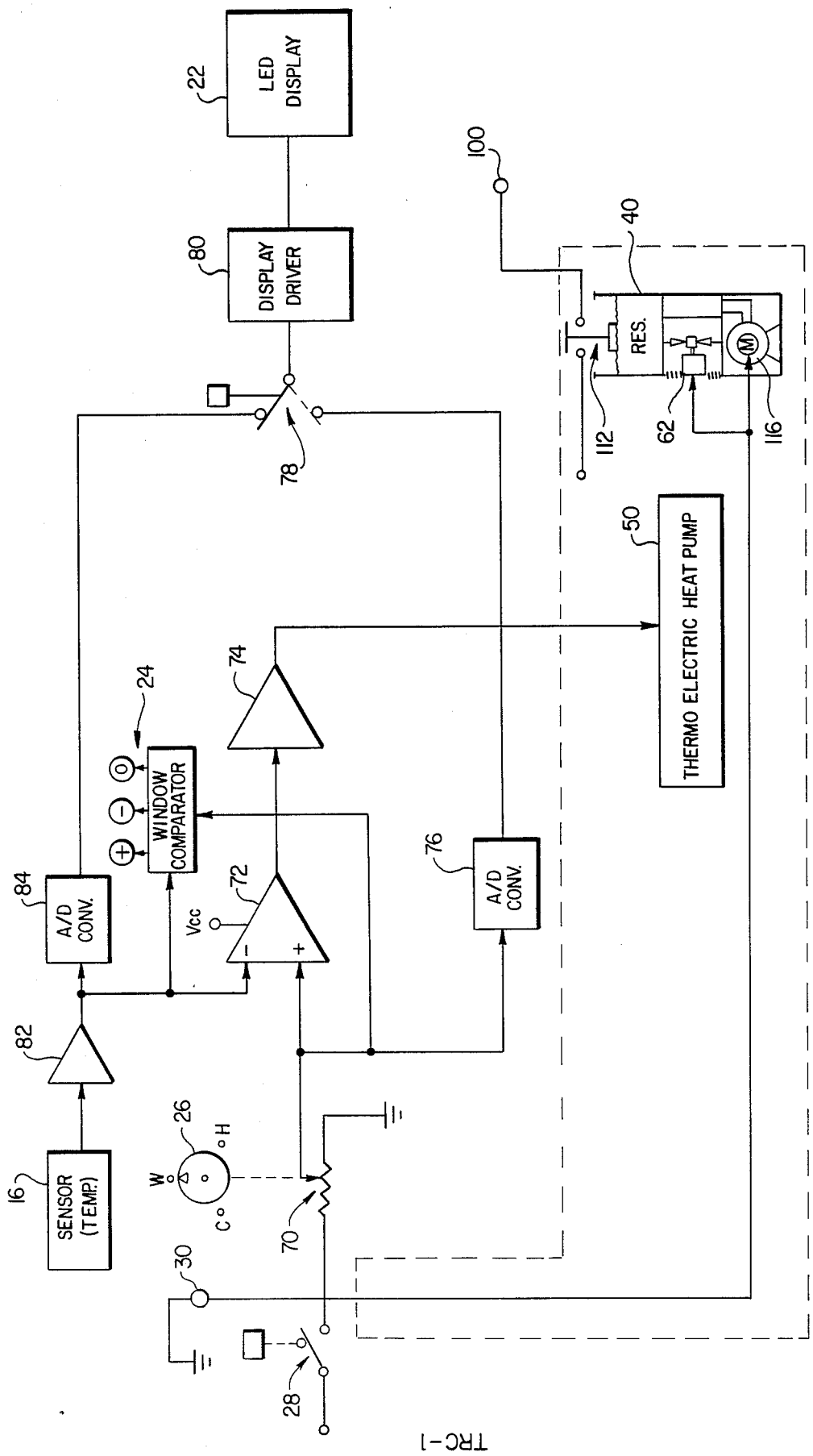
Figure 3C:
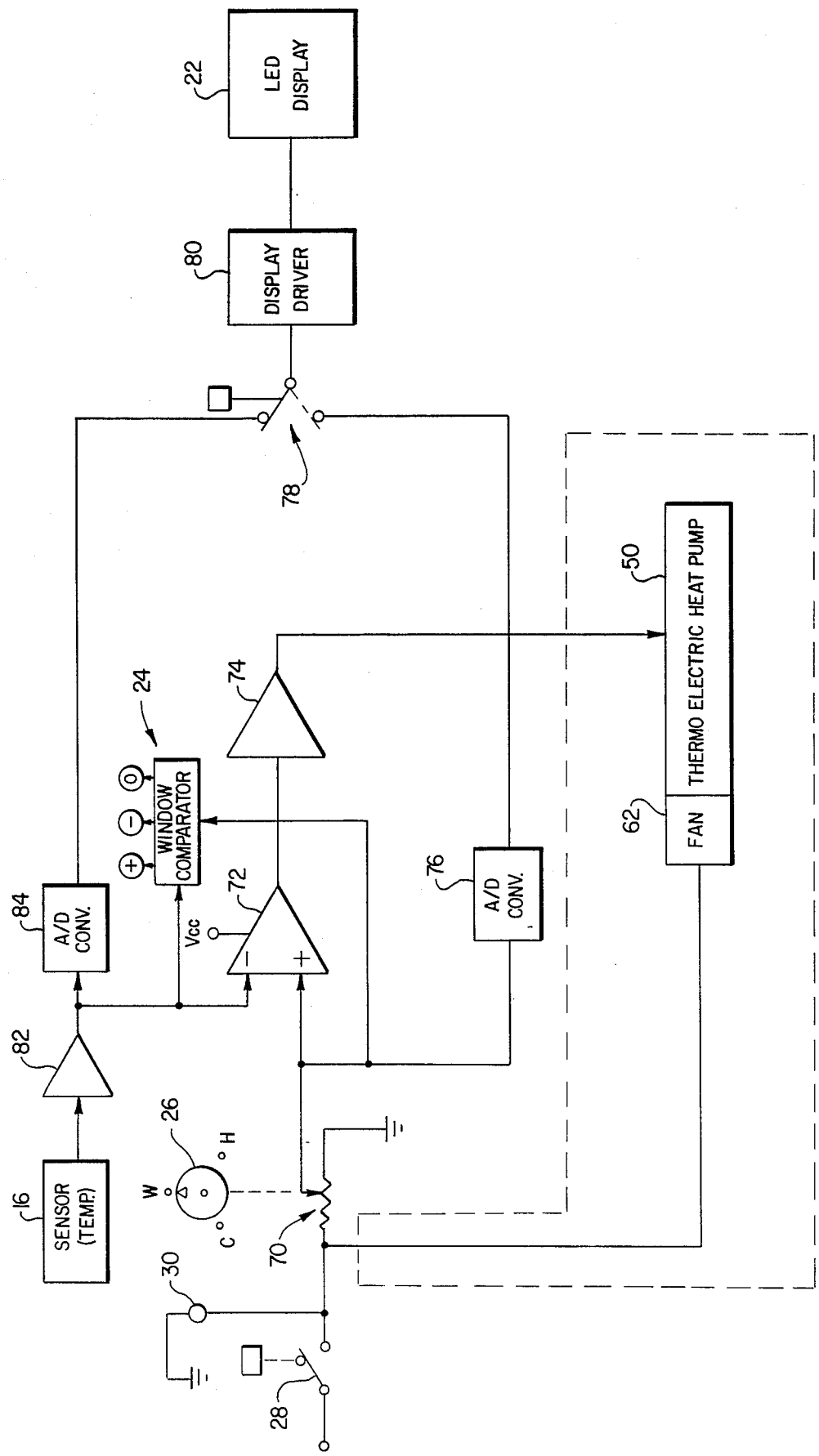

Referring now to FIGS. 3a-3c, FIG. 3a discloses circuitry for the hot/cold therapy device using the first embodiment of the hot/cold assembly 36. A source of power is connected to switch 28. Switch 28 is connected to the junction of the motor of fan 62, a power on indicating light emitting diode 30, and resistor of temperature selection potentiometer 70. The arm of potentiometer 70 is connected for adjustment by the temperature selection dial 26 for selecting the desired temperature setting, and to the junction of the positive terminal of a differential amplifier 72, an analog to digital converter (ADC) 76, and a window comparator 24 which may be, for example, a specialty integrated circuit manufactured by Burr Brown Incorporated. The ADC is connected to one side of a two way switch 78. The two way switch has its pole connected to a display driver 80 for driving the display 22. The temperature sensing transducer 16 has its output connected to an amplifier 82. Amplifier 82 amplifies the analog sensor signal to a working level. The amplifier 82 is connected to the junction of an analog to an ADC 84, window comparator 24, and to the negative terminal of the differential comparator 72. The ADC 84 is connected to the second side of the two way switch 78. The two way switch 78 is operable by a mechanical switch 23 with or without locking means to connect either the temperature setting digital signals or the actual temperature digital signals to the display driver 80 for display by the display 22. The differential comparator outputs a zero, positive, or negative voltage to the junction of the driver of the temperature status indicator 24 and to an amplifier 74. Amplifier 74 is connected to the thermoelectric heat pump 50 for driving the thermoelectric heat pump with a polarity for either heating or cooling the pad to the temperature setting.

The circuitry (FIG. 3c) for the hot/cold device 10 using the second embodiment of the hot/cold assembly 36 (FIG. 2b) is identical to that of FIG. 3a except that the fan 62 is located in the housing 40 of the hot/cold assembly 36. While, the circuitry for the heat pipe type hot/cold assembly 36 (FIG. 2c) is substantially that of the FIG. 3a circuitry except that the heat pipe 66 replaces the fluid cooling system entirely.

SECOND EMBODIMENT OF THE HOT/COLD THERAPY APPARATUS

Figure 4:
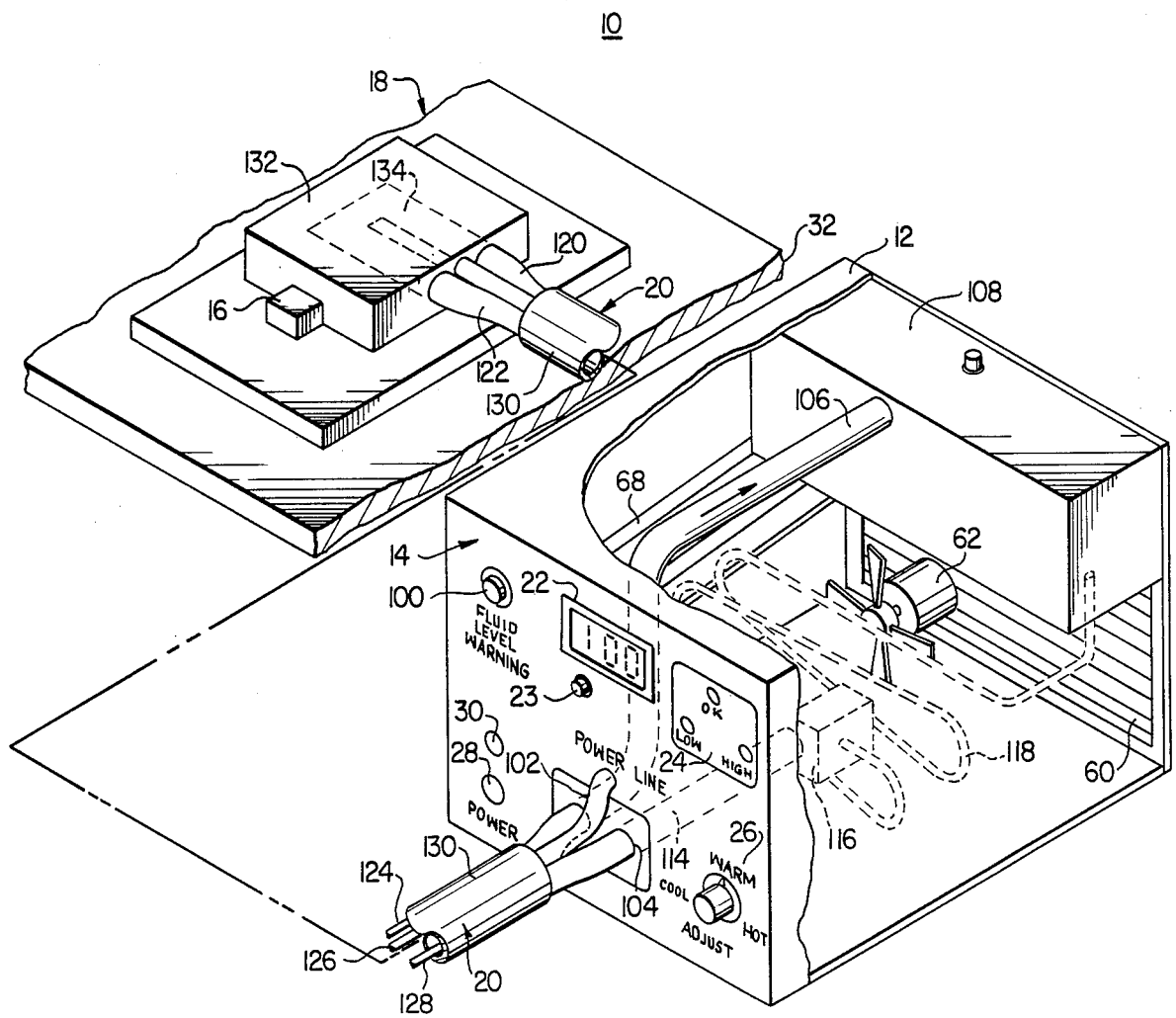
FIG. 4 is an isometric view of the control unit with a portion of the housing broken away to show interior details.

Referring now to FIG. 4, a second embodiment of the hot/cold therapy apparatus is shown with like numbers used to reference parts common to the parts of the first embodiment's structure. Thus, the device 10 includes a control box 12 with a control panel 14 formed thereon. A temperature sensor 16 and a thermal pad assembly 18. The hot/cold therapy pad assembly 18 is connected by an umbilical line 20 to the control box 12.

The control panel 14 includes a temperature display 22 having a press button switch 23 for selecting either the operating temperature of the pad 32 of the hot/cold therapy pad assembly of the temperature operation setting. A temperature status indicator 24 displays the operating temperature status during operation, and an operating temperature selection dial 26 is provided for setting the desired operation temperature. A fluid level warning indicator 100, which may be a light emitting diode, for example, is provided for indicating an unacceptable reservoir liquid level. A power ON/OFF switch 28 together with a power on indicator 30 completes the electrical portion of the panel 14. Liquid connectors 102 and 104 are mounted in the housing 14.

Connector 102 is connected by a conduit 106 to a closed reservoir 108 for returning liquid from the therapy pad assembly 36. The reservoir has a filling aperture for filling the reservoir with a liquid such as water for a purpose hereinafter described. The reservoir 108 is equipped with either an electro/mechanical water level gauge 112 (FIG. 3b) connected to the fluid level warning indicator 100 (FIG. 4) or an electronic liquid level sensor for indicating when the fluid level is unacceptably low. The connector 104 is connected by a conduit 114 to the outlet of a motor driven pump 116 having its inlet connected to the outlet of a radiator 118. The pump 116 and radiator 118 are shown in phantom to indicate their absence in the first embodiment. The radiator 118 has its inlet connected to the reservoir for receiving the liquid. A fan 62 is positioned with respect to the radiator 118 to blow air at ambient through the radiator. Grills 60 and 68 are provided in the housing 12 to accommodate air flow into and out of the housing.

The umbilical line 20 includes flexible liquid conduits 120 and 122, and electrical leads 124 and 126 for the thermoelectric heat pump 50 and lead 128 for the temperature sensor 16 output; the conduits and leads are mounted in a flexible sleeve 130. The conduits have ends equipped with mating connectors for connection to the in and out connectors 102 and 104 of the housing 12.

The hot/cold therapy pad assembly 36, is substantially that disclosed in FIG. 2a, the only difference is that the finned heat sink 56 has been replaced by a block 132 of conductive material such as copper. The block has walls forming a passage 134 with bosses (FIG. 4) to which are fixed the flexible connectors 120 and 122 of the umbilical line. The electrical leads 124 and 126 are connected to the thermoelectric heat pump elements, and the electrical lead 128 is connected to the temperature sensor.

The electrical circuit for the second embodiment is shown in FIG. 3b, which is substantially that of Figure 3a modified to include power for the liquid pump 116 and the fluid level indicator 100 when the electro/mechanical switch 112 is closed. It will be appreciated by one skilled in the art that an electronic switch can be used in place of the electro-mechanical switch. Thus, the source of power is connected to the ON/OFF switch 28. The ON/OFF switch 28 is connected to the junction of switch on indicator 30, temperature selector potentiometer 70, motors of centrifugal pump 116 and fan 62, and to a terminal of the switch of the electro/mechanical gauge 112. When the ON/OFF switch is closed power flows: to turn on the power status indicator 30, to the resistor of the potentiometer, to run the motor of the centrifugal pump 116, to run the fan motor of the fan, and when the electro/mechanical switch 112 is closed owing to a low water level, to turn on the fluid level warning indicator.

The pickoff arm of the potentiometer is activated mechanically by the temperature setting dial 26, and a voltage indicative of the temperature selection is connected to the junction of an ADC 76 and the positive terminal of differential amplifier 72. The ADC 76 is connected to the first side of a two way switch 78. The temperature sensor 16 is connected to an amplifier 82 to amplify the sensor voltage to a working level. The amplified output of amplifier 82 is connected to the junction of ADC 84 and the negative terminal of the differential comparator 72. The ADC 84 is connected to the second side of the switch 78. The pole of switch 78 is connected to a display driver 80 and the display driver is connected to the temperature display 22. The switch 78 is normally in contact with the second side of switch 78 to input digital signals of the sensor's ADC representative of the hot/cold pad temperature through the display driver to the display for display, and is spring loaded so that when pressed to contact the first side the temperature setting digital signals of the ADC pass through the display driver to the LED display for display.

The positive, negative, or zero voltage output of the differential amplifier 72 is connected to the junction of the temperature status indicator 24 and an amplifier 74. The amplifier 74 amplifies the output of the differential comparator to provide a signal of the proper polarity to the terminals of the thermoelectric heat pump for selectively cooling or heating the pla,the in contact with the heating pad. The liquid in the heat sink block acts as a carrier for either supplying energy or removing energy to maintain the temperature of the heat sink at a working level.

Figure 5A:
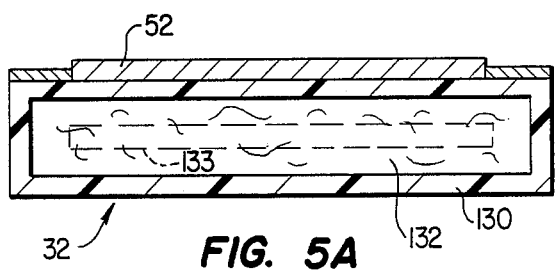
FIGS. 5a-5c are sectional views of pad constructions of the hot/cold therapy device constituting the subject matter of the invention.
Figure 5B:
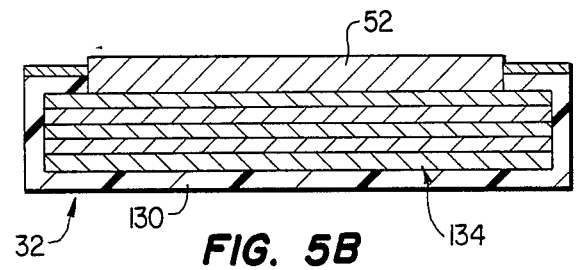
Figure 5C:
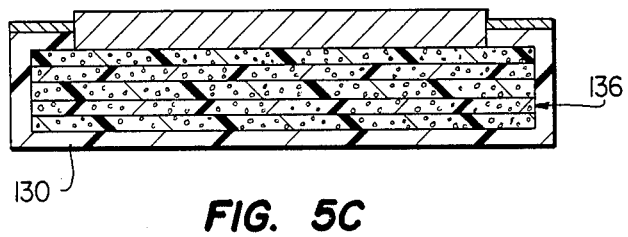

Referring now to FIGS. 5a-5c for descriptions of preferred pad 32 constructions for the above described embodiments. The purpose of the heat transfer pad is to provide uniformly heated or cooled area(s) which are typically larger than the cooling surface of the thermoelectric module. Further the heat transfer pad or wrap may be characterized as being bendable or shapable to closely conform to the contours and irregular shapes as on a patient's or animal's body parts or limbs.

Two basic types and a combination thereof are envisioned for "spreading" the heating or cooling effect throughout the pad. The first type of pad 32 (FIG. 5a) is a convective pad which includes the pad 130 in good thermal contact with the plate 52 of the thermoelectric heat pump 50. A gel, liquid, or other heat transfer substance 132 is contained in the pad 130 in either direct or indirect contact with the thermal module plate 52. A suitable gel is that sold under the trademark HYPOL by W. R. Grace Company.

In a second embodiment (FIG. 5b), the pad 32 is a conductive pad which includes the pad 130 filled with layers 134 of thermally conductive flexible single, laminated, or braided sheets of metal, plastic, rubber, fabric or the like material in direct contact one to another, and with the top layer in direct contact with the cold plate 52 or the flexible copper plate 34 or both. The layers of the material are each about two mils thick and five layers are preferred. Thus, the total thickness of the layers is about ten mils.

In a third embodiment (FIG. 5c), the pad 130 is filled with plastic layers 136 impregnated with metal particles. Again five layers each having a two mil thickness are preferred, although a ten mil thick block of the metal impregnated plastic material can be used with satisfactory results.

It will be appreciated by those skilled in the art that the convection and conduction types can be combined to form a fourth embodiment. Thus, the pad 130 can be filled with a thermally conductive gel, liquid, fluid or the like and a thermally conductive flexible structure 133 shown in phantom in FIG. 5a of material immersed or embedded therein.

The preferred pad 32 is a laminated structure of highly conductive thin metal (copper) sheets coated with a soft pliable thermally conductive boron nitride filled rubber. Such a material is that sold under the trademark CHOTHERM by Chomerics Incorporated. The laminated structure is preferred to provide sufficient pad crosssectional area for uniform heat transfer while maintaining bendability and flexibility in the overall structure. The cover 38 for the pad 32 may be a disposable cover. Also the pad 130 when removably attached to the laminated metal structure embodiments may be disposable.

In operation of the hot/cold therapy device 10 (FIG. 1), the device 10 is connected to a standard 120 V, 60 Hz ac power supply or to a dc power supply. The power ON/OFF switch 28 is pressed to the on position, which position is indicated by the activation of the switch status indicator 28. The desired temperature is set by turning the temperature select/adjust dial 24 to the desired temperature setting, pressing the temperature display selection switch 23, and observing the temperature setting displayed on the display 22. The pad assembly 18 is attached to the patient. The temperature status monitor then indicates whether the temperature of the pad is at or above or below the set temperature, and the display 22 displays the pad's actual temperature. The system instantaneously directs an increase or decrease in power to the thermoelectric module for a temperature correction. The pad, after about a two minute lead time, reaches the set temperature. The set temperature can be adjusted using the temperature control/adjust dial 26 for fine tuning the desired temperature setting.

Although several embodiments of the invention have been described, it will be apparent to a person skilled in the art that various modifications to details of construction shown and described may be made without departing from the scope of this invention.

What is claimed is:

1. A temperature controlled hot/cold producing pad comprising:
    a therapeutic pad;
    a hot/cold producing means mounted on the pad, said means having first and second opposing sides with the first side in thermal contact with the pad;
    means in operative association with the second side of the hot/cold producing means for maintaining a working temperature difference at the second opposing end of the hot/cold producing means;
    a temperature sensing means connected to the therapeutic thermal pad for sensing the pad's temperature;
    a conduit means including electrical leads connected to the hot/cold producing means and temperature sensing means; and
    a control means connected to the electrical leads for controlling operation of the temperature controlled hot/cold therapeutic pad;
    wherein the hot/cold producing means having first and second opposing sides includes a thermoelectric heat pump, and wherein the means in operative association with the second side of the opposing sides for maintaining a working temperature difference at the second opposing side includes a liquid cooled heat sink in thermal contact with the second hot/cold plate, said liquid cooled heat sink including a block of thermal conductive material with walls forming a passage for flowing liquid through the block for maintaining the operative temperature difference, the conduit means including first and second flexible conduits connected to the passage, and the control means includes a reservoir connected to the first flexible conduit for receiving and storing a liquid coolant, a radiator connected to the reservoir, a pump connected to the reservoir and to the second conduit means for pumping the liquid coolant from the reservoir through the radiator for heating extraction, second conduit, heat sink passage and return through the first conduit to the reservoir.

2. A termperature controlled hot/cold producing pad according to claim 1 wherein the therapeutic pad is removably attached to the hot/cold producing means wherein the hot/cold producing means is adapted for use with disposable type therapeutic pads.

3. A temperature controlled hot/cold therapeutic pad according to claim 1 wherein the control means includes a circuit means having an ON/OFF switch means for connection to a power source for selectively supplying operating power through the electrical leads to the hot/cold producing means, a temperature setting and adjust means connected between the switch and hot/cold producing means for selecting and adjusting the selected operating temperature, a temperature status indicating means connected to an electrical lead to the temperature sensing means and temperature setting means for indicating the above, below, or at temperature setting, and a display means selectively connected to the temperature setting and adjust means and temperature sensing means lead for selectively displaying the set or actual temperature.

4. A temperature controlled hot/cold therapeutic pad according to claim 1 further including a thermally conductive flexible plate operatively associated with the first side of the hot/cold producing means for forming a thermal extension of the first side.

5. A temperature controlled hot/cold therapeutic pad comprising:
   a thermoelectric heat pump element sandwiched between first and second hot cold plates, a hot/cold thermal pad means including a pad operatively connected to the first hot/cold plate, said pad having a thermally conductive plate means for forming an extension of the first hot/cold plate of the thermoelectric heat pump for substantially uniform distribution of the hot/cold plate output to the pad, means including a heat sink connected to the second hot/cold plate for maintaining a temperature difference between the second hot/cold plate and heat sink, a temperature sensing means connected to the pad for sensing the pad's temperature, and a control means connected remote to the thermoelectric heat pump, temperature sensing means and means for maintaining a temperature difference between the second hot/cold plate and heat sink for controlling operation of the temperature controlled hot/cold thermal pad; and
   wherein the heat sink of the means including a heat sink connected to the second hot/cold plate is a block of thermal conductive material having walls forming a passage for a coolant for maintaining a temperature difference between the heat sink and second hot/cold plate, first and second conduits connected, respectively, to first and second ends of the passage, a reservoir mounted in the control means for containing the coolant, and means for circulating the coolant through the first conduit, and passage and return of the coolant through the second conduit to the reservoir.

6. A temperature controlled hot/cold therapeutic pad according to claim 5 wherein the means for circulating the coolant includes a pump for pumping the coolant from the reservoir, through the conduits, heat sink passage, and return to the reservoir.

7. A temperature controlled hot/cold therapeutic pad according to claim 6 wherein the means for circulating the coolant includes a radiator connected between the reservoir and pump and a fan in operative association with the radiator for cooling the coolant passing trough the radiator substantially to its working level.

8. A temperature controlled hot/cold therapeutic pad according to claim 5 wherein the control means includes means connected to the temperature sensing means for determining the actual temperature of the pad.

9. A temperature controlled hot/cold therapeutic pad according to claim 8 further including means connected to the thermoelectric heat pump for setting a preselected pad operating temperature, and comparison means connected to the temperature sensing means and temperature setting means for comparing the temperature difference there between and outputting control signals to control the operation of the thermoelectric heat pump to maintain the preselected temperature.

10. A temperature controlled hot/cold therapeutic pad according to claim 9 further including a display means for selectively displaying the actual pad temperature and the set temperature.

11. A temperature controlled hot/cold therapeutic pad according to claim 5 further including a removable cover for the pad of the hot/cold thermal pad means, said pad and removable cover having corresponding patches of synthetic material which adhere when pressed together to fasten the removable cover to the pad.

12. A hot/cold therapeutic apparatus comprising:
    a hot/cold pad assembly means for connection to a temperature control assembly, a temperature control assembly means adapted for carriage by a portable supporting structure for controlling operation of the therapeutic apparatus, and a conduit means including a flexible air conduit and electrical leads for connecting the hot/cold pad assembly to the temperature control means;
    said hot/cold pad assembly means including a pad having a preselected size for attachment to a preselected body portion, a hot/cold pate attached to the pad for heating or cooling the pad, a thermoselectric heat pump connected to the electrical leads of the conduit means and having first and second opposing sides, the first opposing side being connected to the hot/cold plate and the second opposing side forming a finned heat sink, a louvered housing for enclosing the finned heat sink, said louvered housing means being connected in open communication to the air conduit of the conduit means; and
    said temperature control assembly means including a louvered control box having an air passage with first and second open ends, a control means including means for controlling operation of the thermoelectric heat pump and a fan control means for controlling the operation of a fan means, and a fan means connected to the control means, said fan means having a fan mounted in the passage between the first and second ends of the air passage, the first end of the air passage in open communication with the louvers of the louvered control box and the second end connected in open communication with the air conduit means, said fan being operative either to draw air at ambient temperature through the louvers of either the louvered housing means or the louvered control box, air conduit, air passage, across the fins of the finned heat sink and to force the air out either the louvers of the louvered control box or the louvered housing depending on the direction of fan rotation, wherein the size and weight of the hot/cold pad assembly is substantially reduced while maintaining the finned heat sink substantially at ambient.

13. A hot/cold therapeutic apparatus comprising:
    a hot/cold pad assembly means for attachment to a temperature control assembly means, and a temperature control assembly means adapted for carriage by a portable supporting structure and including a control means for controlling operation of the therapeutic apparatus;
    said hot/cold pad assembly including a pad having a preselected size for attachment to a preselected body portion, a hot/cold conductive plate connected to the pad and a flexible heat pipe interconnecting the hot/cold pad assembly means and the temperature control assembly, said flexible heat pipe having a cold/hot end connected to the hot/cold conductive plate and a finned hot/cold end;

said control box means including a louvered housing, an air chamber in open communication with louvers of the louvered housing, and a fan means connected to the control means, said fan means including a fan mounted in the air chamber, said finned hot/cold end of the heat pipe mounted in the air chamber adjacent to the fan wherein air is drawn by the fan through louvers of the louvered housing, across the finned hot/cold end of the heat pipe and forced out louvers of the louvered housing to maintain the finned hot/cold end substantially at ambient temperature.

* * * * *